United States Patent [19]

O'Neil et al.

[11] Patent Number: 5,637,087

[45] Date of Patent: Jun. 10, 1997

[54] PREFILLED, TWO-CONSTITUENT SYRINGE

[75] Inventors: John A. O'Neil, Mundelein; John M. Hofstetter, Vernon Hills, both of Ill.

[73] Assignee: Abbott Laboratories, Abbott Park, Ill.

[21] Appl. No.: 408,767

[22] Filed: Mar. 22, 1995

[51] Int. Cl.⁶ .................................. A61M 37/00
[52] U.S. Cl. ..................... 604/82; 604/86; 604/87; 604/88
[58] Field of Search ................ 604/82–92, 132, 604/185, 191, 200–206, 212, 214, 217, 234, 244–247, 410, 411, 412, 413, 414, 416, 232; 222/92, 93, 95, 82, 83, 145.1, 326, 327, 386; 221/64, 65

[56] References Cited

U.S. PATENT DOCUMENTS

| | | | |
|---|---|---|---|
| 2,153,594 | 4/1939 | Saffir | 604/232 X |
| 3,477,432 | 11/1969 | Shaw . | |
| 3,785,379 | 1/1974 | Cohen | 604/88 |
| 4,136,801 | 1/1979 | Pavenick | 222/82 |
| 4,886,495 | 12/1989 | Reynolds | 604/88 |
| 4,936,841 | 6/1990 | Aoki et al. | 604/413 |
| 4,957,637 | 9/1990 | Cornell . | |
| 5,088,996 | 2/1992 | Kopfer et al. . | |
| 5,156,598 | 10/1992 | Skakoon et al. | 604/192 |
| 5,158,546 | 10/1992 | Haber et al. . | |
| 5,281,198 | 1/1994 | Haber et al. | 604/86 |
| 5,372,586 | 12/1994 | Haber et al. . | |
| 5,423,752 | 6/1995 | Haber et al. | 604/86 |
| 5,474,541 | 12/1995 | Ritsky et al. | 604/213 |
| 5,476,449 | 12/1995 | Richmond | 604/87 |
| 5,569,191 | 10/1996 | Meyer | 604/82 |

*Primary Examiner*—Robert A. Hafer
*Assistant Examiner*—V. Alexander
*Attorney, Agent, or Firm*—Neal D. Marcus

[57] ABSTRACT

A prefilled, two-constituent system is provided with a syringe barrel having a dispensing end with an inwardly directed, stationary, piercing cannula. Within the syringe barrel is a first, sealed, collapsible container holding a first constituent at subatmospheric pressure. The first container is slidably disposed within the syringe barrel adjacent the piercing cannula. A second, sealed, collapsible container holding a liquid second constituent is slidably disposed within the syringe barrel spaced from the first container. A carrier is slidably disposed within the syringe barrel between the first and second containers. The carrier has a double-ended, hollow, piercing needle with oppositely extending first and second ends for piercing the first and second containers, respectively. A plunger is slidably mounted within the syringe barrel for applying a force to the second container.

16 Claims, 2 Drawing Sheets

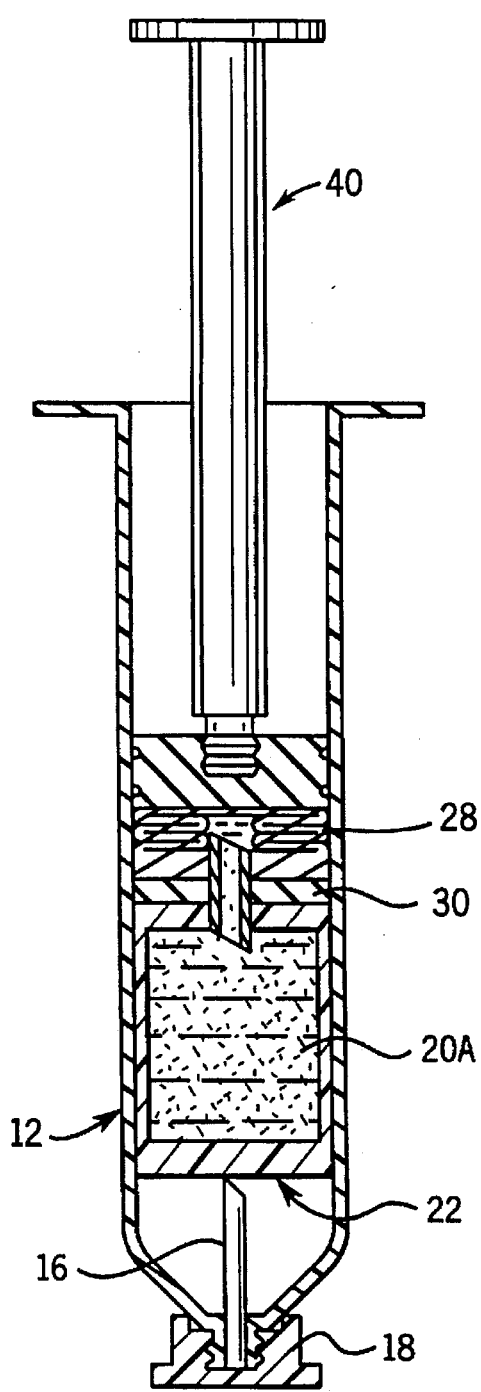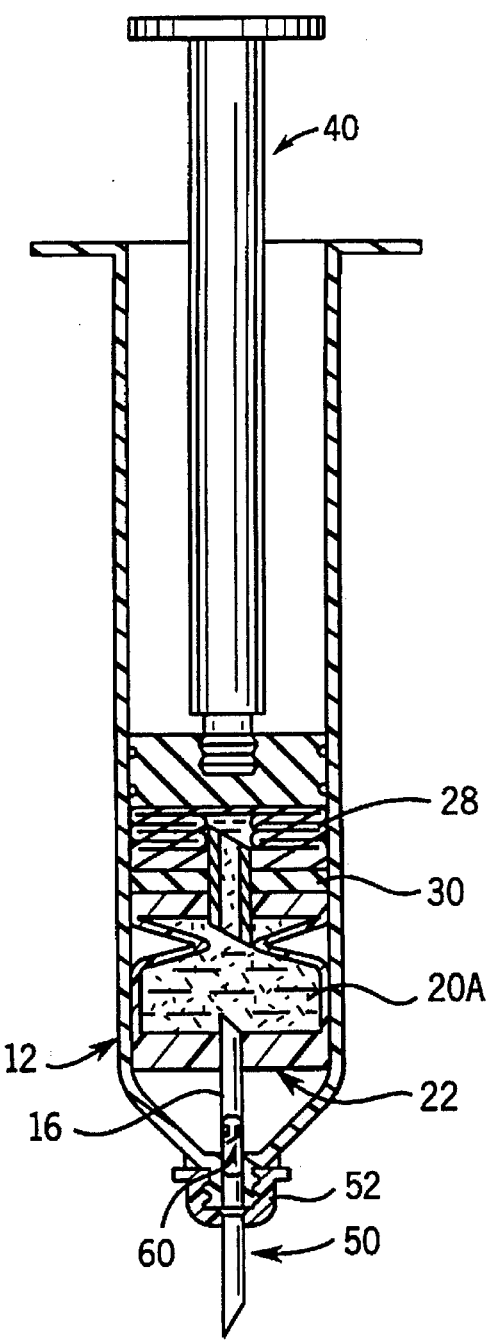

PREFILLED, TWO-CONSTITUENT SYRINGE

TECHNICAL FIELD

This invention relates to a packaging system and dispensing system for two constituents or components that are stored separately in isolation from each other but which must be combined or mixed together prior to dispensing. The invention is particularly suitable for use with a medicament, such as a drug in powder form, which must be dissolved and diluted in a liquid.

BACKGROUND OF THE INVENTION AND TECHNICAL PROBLEMS POSED BY THE PRIOR ART

In some medical applications, as well as in some industrial applications, it is necessary, or at least preferable, to maintain two components or constituents in isolation prior to combining the two components for subsequent dispensing as a solution, mixture, or other combination.

For example, some pharmaceutical preparations, such as injectable solutions or suspensions of a drug, are not sufficiently stable to accommodate prolonged storage prior to use. However, the components of the solution or suspension may have adequate stability if the components are stored separately prior to being combined.

It would be desirable to provide an improved system that will accommodate the packaging of two such components in isolation from each other, but which can be subsequently operated to combine or mix the components for dispensing.

It would be especially advantageous if such improved system could be employed with two liquid components as well as with at least one concentrated (e.g., powdered) component.

It would be desirable with such a system to positively seal both components from the ambient atmosphere as well as from each other.

It would also be beneficial if such an improved system could be provided in a self-contained form that is compact, portable, simple to manipulate, and readily adaptable to different proportions and dosages of the components.

Additionally, it would be desirable if such an improved system could readily accommodate the storage and administration of a variety of drugs which require reconstitution and/or dilution including, among other types, a medicament in powder form requiring mixing with a diluent, a medicament in a liquid form requiring mixing with a diluent, and a lyophilized compound requiring mixing with a diluent.

The present invention provides an improved packaging and dispensing system which can accommodate designs having the above-discussed benefits and features.

SUMMARY OF THE INVENTION

The present invention provides a prefilled syringe system for storing two components or constituents in isolation from each other. The system can be subsequently operated for combining or mixing the two constituents for then dispensing the combination. The syringe system employs a straight-through design so that the syringe plunger need be pushed only in one direction.

The syringe system includes a syringe barrel having a dispensing end with an inwardly directed, stationery, piercing cannula communicating through the dispensing end to accommodate the dispensing of fluid from the syringe barrel.

A first component or constituent (e.g., a liquid or solid medicament) is sealed at subatmospheric pressure in a first, collapsible container. The first container is slidably disposed within the syringe barrel adjacent the stationary piercing cannula.

A liquid, second constituent, such as a diluent liquid, is sealed in a second, collapsible container. The second container is slidably disposed within the syringe barrel spaced from the first container.

A carrier is slidably disposed within the syringe barrel between the first and second containers. The carrier has a double-ended, hollow, piercing needle having oppositely extending first and second ends for piercing the first and second containers, respectively.

A plunger is slidably mounted within the syringe barrel for applying a force to the second container. In operation, as the plunger contacts the second container and moves it toward the first container, the second container is first pierced with the carrier needle second end. The first container is then pierced with the carrier needle first end. Next, the second container collapses while discharging the liquid constituent into the first container. The first container is then pierced with the cannula, and the first container collapses while dispensing the first container contents.

Numerous other advantages and features of the present invention will become readily apparent from the following detailed description of the invention, from the claims, and from the accompanying drawings.

BRIEF DESCRIPTION OF THE DRAWINGS

In the accompanying drawings that form part of the specification, and in which like numerals are employed to designate like parts throughout the same.

FIGS. 2–5 are views similar to FIG. 1, but FIGS. 2–5 illustrate sequential steps in the actuation or operation of the syringe system.

DESCRIPTION OF THE PREFERRED EMBODIMENT

While this invention is susceptible of embodiment in many different forms, this specification and the accompanying drawings disclose only one specific form as an example of the invention. The invention is not intended to be limited to the embodiment so described, however. The scope of the invention is pointed out in the appended claims.

Figures illustrating the apparatus show some mechanical elements that are known and that will be recognized by one skilled in the art. The detailed descriptions of such elements are not necessary to an understanding of the invention, and accordingly, are herein presented only to the degree necessary to facilitate an understanding of the novel features of the present invention.

Figure 1:
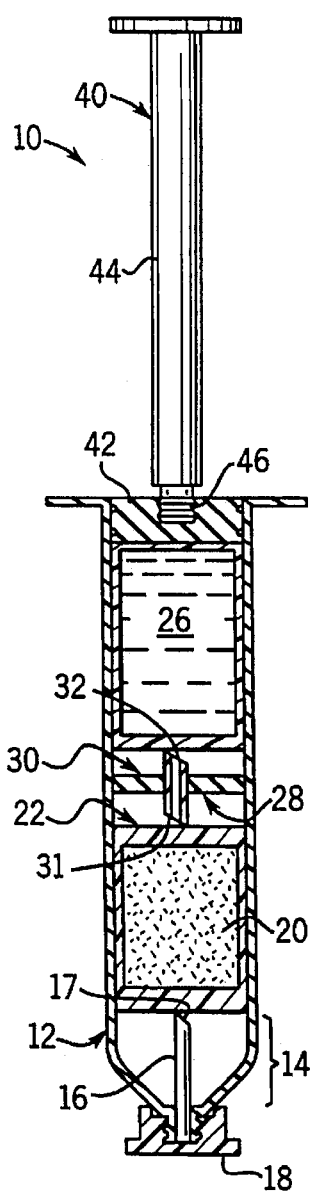
FIG. 1 is a partially cross-sectional view of the syringe system of the present invention.
Figure 1A:
FIG. 1A is a side elevational view of the container of the liquid constituent.
Figure 2:
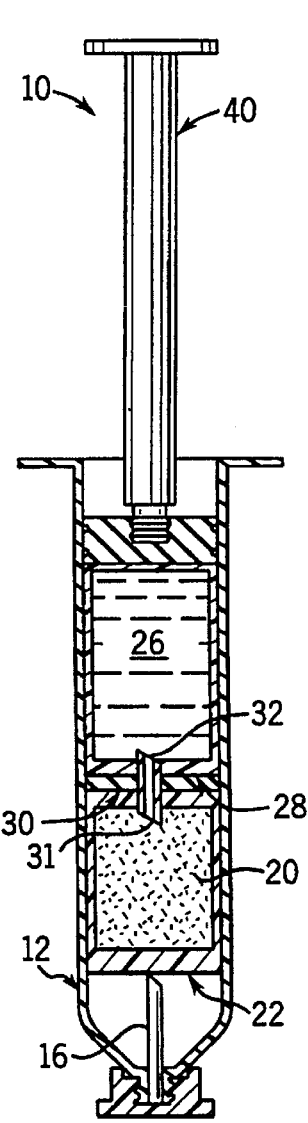

The prefilled syringe system of the present invention is illustrated in FIG. 1 and is designated generally therein by the reference number 10. The system includes a syringe body or barrel 12. The barrel 12 has a dispensing end 14 with an inwardly directed, stationary, piercing cannula 16 communicating through the dispensing end 14 to accommodate the dispensing of fluid from the syringe barrel 12.

It will be appreciated that the cannula 16 may be a conventional, hollow, tubular member with a sharp point 17, and the syringe barrel distal end 14 is molded around, or otherwise fixedly engages, a portion of the cannula 16.

Prior to dispensing any fluid, the syringe barrel dispensing end 14 is typically capped, as with a cap 18. Cap 18 can be provided with a thread form, such as is employed in connection systems marketed under the trademark LUER-LOK. To this end, the syringe body can be provided with a mating thread form for accommodating threaded engagement with the cap 18. Any other suitable conventional or special capping systems may be employed.

A concentrated component or constituent 20 is sealed in a first, collapsible container 22. It is presently contemplated that in the preferred embodiment the container 22 may be fabricated from a synthetic polymer, such as a thermoplastic material.

The constituent 20 is sealed within the container 22 in a subatmospheric condition. The constituent 20, in the preferred contemplated embodiment for use in medical applications, can be a drug or other medicament in granular form, powder form, or other particulate form. It is contemplated that the constituent 20 sealed in the container 22 would typically be a drug which, if in solid form, requires reconstitution, or if in liquid form, requires dilution. Thus, the system of the present invention will be useful in the containment of hazardous drugs such as are used in oncological applications or in biotechnology delivery applications.

A second constituent 26, in the form of a liquid, is sealed within a second, collapsible container 28. The liquid constituent 26 would typically be a diluent for diluting and/or reconstituting the first constituent 20. The container 28 is also collapsible. It may be formed from the same synthetic polymer materials as used for the first container 22.

Both containers 22 and 28 are slidable within the syringe barrel 12. Preferably, each container 22 and 28 is initially installed within the syringe barrel 12 in a manner which establishes some resistance to sliding movement at one or more axial locations within the syringe barrel 12. The resistance to sliding movement associated with each container is of a predetermined, but different, value at selected axial locations in the barrel 12. The predetermined resistance to sliding requires that a predetermined amount of axial force must be imposed on each container in order to initiate sliding movement of the container along the syringe barrel 12. This sliding resistance can be established with a suitable friction fit, or with internal, frangible, breakaway tabs (not illustrated), or with mating groove and ring formations (not illustrated) which must be disengaged upon the application of the predetermined force in order to permit subsequent sliding movement. Other suitable special or conventional systems for establishing a predetermined level of resistance to initial sliding motion may be employed.

The second container 28 is spaced from the first container 22. Between the two containers is a carrier 30 which is slidably disposed within the syringe barrel 12. The carrier 30 has a double-ended, hollow, piercing needle having a first end 31 for piercing the top of the first container 22 and having an oppositely extending second end 32 for piercing the bottom of the second container 28. Preferably, the double-ended needle is made of a suitable metal such as steel.

The carrier 30 is slidable within the syringe barrel 12 toward the first container 22. However, the carrier 30 cannot slide within the syringe barrel 12 until a predetermined amount of axial force is applied to the carrier 30. Such a predetermined resistance to sliding may be effected with a suitable friction fit between the carrier 30 and the syringe body 12. Alternatively, appropriate, frangible, breakaway tabs may be employed (not illustrated) or mating ring and groove structures may be employed (not illustrated).

A plunger 40 is provided for operating the system. The plunger 40 includes a piston 42 slidably received within the syringe barrel 12.

The piston 42 is preferably initially located in contact with the upper end of the second container 28 as illustrated in FIG. 1. For packaging convenience, the plunger 40 may be provided with a shank 44 having a threaded end or snap-fit end 46 for engaging a mating thread form or snap-fit form in the top of the piston 42. Such a structure permits packaging the system components with the plunger shank 44 not initially connected or assembled with the piston 42. When it is subsequently desired to use the system, the user can thread or snap-fit the shank 44 into the piston 42.

The operation of the packaging system syringe 10 will next be described with reference to the sequential operational steps illustrated in FIGS. 2–5. In the first stage of the operation illustrated in FIG. 2, the plunger 40 is initially subjected to sufficient force to overcome the initial resistance force holding the second container 28 at its highest elevation. The second container 28 is forced downwardly against the carrier needle end 32. The force is sufficient to move the carrier 30 from its initial position (FIG. 1) to a slightly lower position (FIG. 2) wherein the carrier needle first end 31 is moved against, and occluded by, the upper end wall of the first container 22.

Continued downward movement of the plunger 40 causes the second container 28 to move downwardly relative to the carrier. The bottom end wall of the second container 28 is then pierced by the carrier needle second end 32 as continued force is applied to the plunger 40.

The first container 22 is initially held with sufficient force in its initial position (FIGS. 1 and 2) to prevent it from being moved downwardly in the syringe barrel 12 as the carrier needle first end 31 is forced against it and as the second container 28 is penetrated by the carrier needle second end 32. Further, the force required to penetrate the bottom end of the second container 28 with the needle end 32 is less than the force required to penetrate the upper end of the first container 22 with the needle end 31. Thus, the bottom end wall of the second container 28 is completely penetrated by the carrier needle end 32 while the upper end wall of the first container 22 occludes, but is not penetrated by, the carrier needle first end 31. Thus, there is no danger that the first container liquid constituent 26 could leak out of the needle end 31 into the space above the upper end wall first container 22.

Further, even if the carrier needle first end 31 is not occluded by the upper end wall of the first container 22, there is little likelihood that any significant amount of the liquid constituent 26 could be initially expelled from the second container 28 as the lower end of the second container 28 is being penetrated by the carrier needle end 32. This is because the second container 28 is not yet subjected to sufficient force to collapse it and expel the liquid constituent 26, and there is no vent system that would admit ambient air into the second container 28 so as to permit the liquid constituent 26 to run out solely under the influence of gravity. Absent such venting, the liquid constituent 26 remains in the second container 28 and is not be able to flow out through the carrier needle (ends 32 and 31) even if the needle first end 31 is completely unobstructed.

Figure 3:
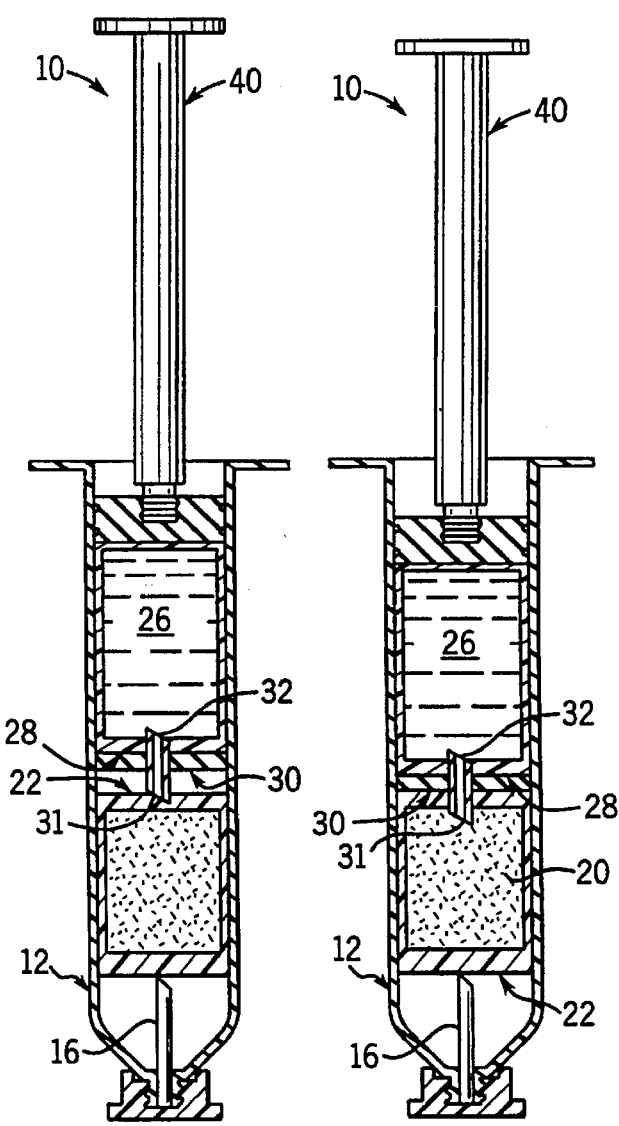
Figure 1B:
FIG. 1B is a side elevational view of the container of the other constituent.

Next, additional force is applied to the plunger 40. As illustrated in FIG. 3, the additional force is sufficient to cause the carrier needle first end 31 to penetrate the upper end wall of the first container 22 and to move the second container 28 and carrier 30 to a lower position in which the carrier 30 abuts the upper end wall of the first container 22.

When the upper end wall of the first container 22 is fully penetrated by the carrier needle first end 31, the liquid constituent 26 can flow from the second container 28 into the first container 22 where it forms a solution with, mixes with, or is otherwise combined with the first constituent 20.

It will be recalled that the first container 22 is manufactured and sealed around the constituent 20 such that the constituent 20 is sealed at subatmospheric pressure within the first container. Thus, when the first container 22 is pierced by the needle first end 31, the subatmospheric pressure within the first container interior assists in drawing the liquid constituent 26 from the second container 28 into the first container 22.

Further, additional force is applied to the plunger 40, and as illustrated in FIG. 4, the force is sufficient to collapse the second container 28 so as to assist in fully expelling the liquid constituent 26 therefrom. In FIG. 4, the resulting combination of the first constituent 20 with the liquid second constituent 26 is designated by the reference characters 20A.

With reference to FIG. 4, it will be appreciated that the force required to collapse the second container 28 is greater than the force required to penetrate the upper end of the first container 22 with the carrier needle first end 31. However, the force required to collapse the second container 28 is less than the force required to effect downward movement of the first container 22. Therefore, as shown in FIG. 4, the first container 22 remains in its original location above, and not yet penetrated by, the cannula 16 as the two constituents in the system are combined when the constituent 26 is forced into the container 22.

In some applications, it may be desirable to insure that the two constituents are fully mixed or otherwise combined. To this end, the syringe barrel 12 can be shaken to insure good mixing.

FIG. 5 illustrates the final steps in the operation of the system. If desired, the syringe barrel cap 18 can be removed, and the syringe barrel 12 can be connected to the receiving component or discharge tubing (not illustrated). Typically, a hollow needle 50 is mounted at the distal end of the syringe barrel 12. The needle 50 may be of a conventional, single-ended type, with a straight, hollow stainless steel shaft, typically 20 gauge in size, provided with a swaged or molded hub 52 for engagement with the bottom, distal end of the syringe barrel 12.

When properly mounted on the syringe barrel 12, the needle 50 is in alignment with the cannula 16, and fluid communication is established between the cannula 16 and needle 50. After the needle 50 is properly mounted on the syringe barrel 12 (or after the syringe barrel is otherwise properly connected to some suitable receiving component), the plunger 40 can be depressed further by applying additional axial force. This causes the first container 22 to collapse and causes the contents to be expelled therefrom through the needle 50.

In a preferred embodiment as shown in FIG. 5, the cannula 16 is provided with a check valve 60 (such as an inserted thermoplastic flapper type valve) to prevent backflow into the system. This check valve may be any suitable conventional or special one-way valve.

The above-described syringe system of the present invention provides an advantageous means for dispensing a combination of two constituents that must be kept separate from each other until they are to be used in combination. The system is self-contained and sealed. Reconstitution or dilution of a drug using this system can be effected at bedside when the drug is needed. The choice of the diluent liquid is not restricted or limited because the system accommodates any diluent compatible with the structural materials employed.

The system permits the constituents to be stored in forms in which the stability of the components is maximized. Because the reconstituted product is used immediately, provisions do not have to be made for refrigeration or other storage procedures which might otherwise be required for certain types of reconstituted products.

The syringe system eliminates the need to provide separate vials and vial-piercing needles which must be individually handled and manipulated. Instead, the containers are packaged by the manufacturer in a single holder (syringe barrel), and the needles and cannulas required for piercing the containers are located entirely within the syringe barrel so as to avoid the possibility of the user being accidentally pricked with one of the needles.

It will be readily apparent from the foregoing detailed description of the invention and from the illustrations thereof that numerous variations and modifications may be effected without departing from the true spirit and scope of the novel concepts or principles of this invention.

What is claimed is:

1. A prefilled syringe system comprising:
    a syringe barrel having a dispensing end with an inwardly directed, stationary, piercing cannula communicating through said dispensing end to accommodate the dispensing of fluid from said syringe barrel;
    a first, sealed, collapsible container that contains a first constituent and that is slidably disposed within said syringe barrel adjacent said stationary piercing cannula;
    a second, sealed, collapsible container that contains a liquid second constituent and that is slidably disposed within said syringe barrel spaced from said first container;
    a carrier that is slidably disposed within said syringe barrel between said first and second containers and that carries a double-ended, hollow, piercing needle having oppositely extending first and second ends for piercing said first and second containers, respectively; and
    a plunger slidably mounted within said syringe barrel for applying a force to said second container.

2. The system in accordance with claim 1 in which said plunger includes a piston and a shank removably mounted in said piston.

3. The system in accordance with claim 1 in which said piercing needle is a unitary steel structure.

4. The system in accordance with claim 1 further including a cap removably mounted to said dispensing end of said syringe barrel.

5. The system in accordance with claim 1 further including a hollow needle mounted on said dispensing end of said syringe barrel in communication with said cannula.

6. The system in accordance with claim 1 in which said first container, said second container, and said carrier are each mounted within said syringe barrel and held with a sufficient force to prevent sliding movement along said syringe barrel when subjected to a force less than a predetermined force, said predetermined force being different for each said container and carrier at axial locations along the length of said syringe barrel.

7. The system in accordance with claim 6 in which said plunger applies a force to said second container to sequentially (1) pierce said second container with said needle second end, (2) pierce said first container with said needle first end, (3) collapse said second container while discharging said liquid second constituent into said first container, (4) pierce said first container with said cannula, and (5) collapse said first container while dispensing the contents of said first container.

8. The system in accordance with claim 4 in which (a) said needle first end is initially moved against, and occluded by, said first container with a force that is less than the force required to pierce said second container with said needle second end, (b) the force required to pierce said second container with said needle second end is less than the force required to pierce said first container with said needle first end, (c) the force required to pierce said first container with said needle first end is less than the force required to collapse said second container, and (d) the force required to pierce said first container with said cannula is greater than the force required to collapse said second container.

9. The system in accordance with claim 1 in which said first, sealed, collapsible container contains a first constituent at subatmospheric pressure.

10. A prefilled syringe system for separately storing a concentrated constituent and a liquid constituent and for subsequently mixing and dispensing a mixture of said constituents, said system comprising:

a syringe barrel having a dispensing end with an inwardly directed, stationary, piercing cannula communicating through said dispensing end to accommodate the dispensing of fluid from said syringe barrel;

a first, sealed, collapsible container that contains a first constituent at subatmospheric pressure and that is slidably disposed within said syringe barrel adjacent said stationary piercing cannula;

a second, sealed, collapsible container that contains a liquid second constituent and that is slidably disposed within said syringe barrel spaced from said first container;

a carrier that is slidably disposed within said syringe barrel between said first and second containers and that carries a double-ended, hollow, piercing needle having oppositely extending first and second ends for piercing said first and second containers, respectively; and a plunger slidably mounted within said syringe barrel for applying a force to said second container to sequentially (1) pierce said second container with said needle second end, (2) pierce said first container with said needle first end, (3) collapse said second container while discharging said liquid second constituent into said first container, (4) pierce said first container with said cannula, and (5) collapse said first container while dispensing the contents of said first container.

11. The system in accordance with claim 10 in which (a) said needle first end is initially moved against, and occluded by, said first container with a force that is less than the force required to pierce said second container with said needle second end, (b) the force required to pierce said second container with said needle second end is less than the force required to pierce said first container with said needle first end, (c) the force required to pierce said first container with said needle first end is less than the force required to collapse said second container, and (d) the force required to pierce said first container with said cannula is greater than the force required to collapse said second container.

12. The system in accordance with claim 10 in which said system further includes a hollow needle mounted on the dispensing end of said syringe barrel in communication with said cannula.

13. The system in accordance with claim 10 in which said system further includes a check valve in flow communication with said piercing cannula to prevent return flow into said first container.

14. The system in accordance with claim 10 in which said first constituent is a concentrate.

15. The system in accordance with claim 14 in which said concentrate is a powder.

16. A prefilled syringe system comprising:

a syringe barrel having a dispensing end with an inwardly directed, stationary, piercing cannula communicating through said dispensing end to accommodate the dispensing of fluid from said syringe barrel;

a first, sealed, collapsible container that contains a first constituent at subatmospheric pressure and that is slidably disposed within said syringe barrel adjacent said stationary piercing cannula;

a second, sealed, collapsible container that contains a liquid second constituent and that is slidably disposed within said syringe barrel spaced from said first container;

a carrier that is slidably disposed within said syringe barrel between said first and second containers, that maintains separation between the said first and second containers and that carries a double-ended, hollow, piercing needle having oppositely extending first and second ends for piercing said first and second containers, respectively; and a plunger slidably mounted within said syringe barrel for applying a force to said second container.

\* \* \* \* \*